United States Patent [19]
Yano

[11] Patent Number: 5,596,377
[45] Date of Patent: Jan. 21, 1997

[54] OPHTHALMIC APPARATUS HAVING THREE DIMENSIONAL CALCULATING MEANS

[75] Inventor: Nobuyuki Yano, Okazaki, Japan

[73] Assignee: Nidek Co., Ltd., Japan

[21] Appl. No.: 297,892

[22] Filed: Aug. 30, 1994

[30] Foreign Application Priority Data

Aug. 31, 1993 [JP] Japan .................................. 5-240336

[51] Int. Cl.⁶ ...................................................... A61B 3/10
[52] U.S. Cl. ............................................ 351/211; 351/208
[58] Field of Search .................................... 351/211, 205, 351/208, 210, 214, 221

[56] References Cited

U.S. PATENT DOCUMENTS 5,381,194  1/1995  Nishio et al. ............................ 351/208

FOREIGN PATENT DOCUMENTS 58-97340  6/1983  Japan .

Primary Examiner—William L. Sikes
Assistant Examiner—Huy Mai
Attorney, Agent, or Firm—Finnegan, Henderson, Farabow, Garrett & Dunner

[57] ABSTRACT

An ophthalmic apparatus in which alignment light is projected on the objected eye, and cornea reflecting images of the alignment light are detected at a first and a second detecting optical systems disposed in different directions respectively and, based on the detected data at the first and the second detecting optical systems, a three-dimensional position of the measured portion is found out by a calculating device.

6 Claims, 5 Drawing Sheets

5,596,377

OPHTHALMIC APPARATUS HAVING THREE DIMENSIONAL CALCULATING MEANS

BACKGROUND OF THE INVENTION

1. Field of the Invention

The present invention relates to an ophthalmic apparatus and more particularly, to an ophthalmic apparatus provided with alignment system to align the apparatus with respect to a predetermined portion in the inside of an eye of an examinee.

2. Description of Related Art

Alignment system in conventional ophthalmic apparatuses is to locate the optical axis of the apparatus coaxially with an examinee's eye, specifically, a visual axis of the eye, and is to position the apparatus so as to provide a predetermined working distance between the same and the eye. Alignment in prior arts would be performed for positioning an apparatus within an acceptable error range to an examinee's eye by assuming the location of the apparatus with respect to the examinee's eye for alignment only.

In the conventional apparatus mentioned above, it is not possible to set a measurement portion (treatment portion) at an optional point in the inside of an examinee's eye. For instance, an apparatus for measuring the extent of opacity of a crystalline lens of an examinee's eye also can not set measurement portions at plural expected points.

If the apparatus is located within an acceptable error range with respect to the examinee's eye, dislocation from a proper point to be measured may be disregarded, and thereby reappearance of the measured portion can not be obtained sufficiently. This can not remove measurement errors caused by difference in measured points. If measurement and observation in a lapse of time at an optional point are carried out through the apparatus, obtained data tend to be greatly short of the reliability.

SUMMARY OF THE INVENTION

The present invention has been made in view of the above circumstances and has an object to overcome the above problems and to provide an ophthalmic apparatus capable of aligning the apparatus at optional points with respect to an examinee's eye, and of providing proper reappearance of measuring portion even in measurement in a lapse of time.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus of this invention for aligning optical systems thereof with an expected portion in the inside of an examinee's eye to examine the eye, the apparatus comprising an observing optical system for observing an anterior portion of the eye, a light projecting optical system for projecting alignment light to a cornea of the eye, a detecting optical system for detecting in two directions the light which is projected from the light projecting optical system and then reflected by the cornea, position calculating means for calculating a three-dimensional position of the apparatus with respect to the eye, based on the detected data at the detecting optical system, signal generating means for generating signals to carry out examination of the eye, and memory means for storing the three-dimensional position of the apparatus with respect to the eye at the time of signal generated at the signal generating means, as well as examination data.

According to the present invention, it is possible to align the optical axes of the optical systems in the apparatus with the optional points in the inside of the examinee's eye, thereby to provide proper reappearance of measuring portion in measurement in a lapse of time.

BRIEF DESCRIPTION OF THE DRAWINGS

The accompanying drawings, which are incorporated in and constitute a part of this specification illustrate embodiments of the invention and, together with the description, serve to explain the objects, advantages and principles of the invention. In the drawings.

DETAILED DESCRIPTION OF THE PREFERRED EMBODIMENTS

A detailed description of preferred embodiments of an ophthalmic apparatus embodying the present invention will now be given referring to the accompanying drawings.

Figure 1:
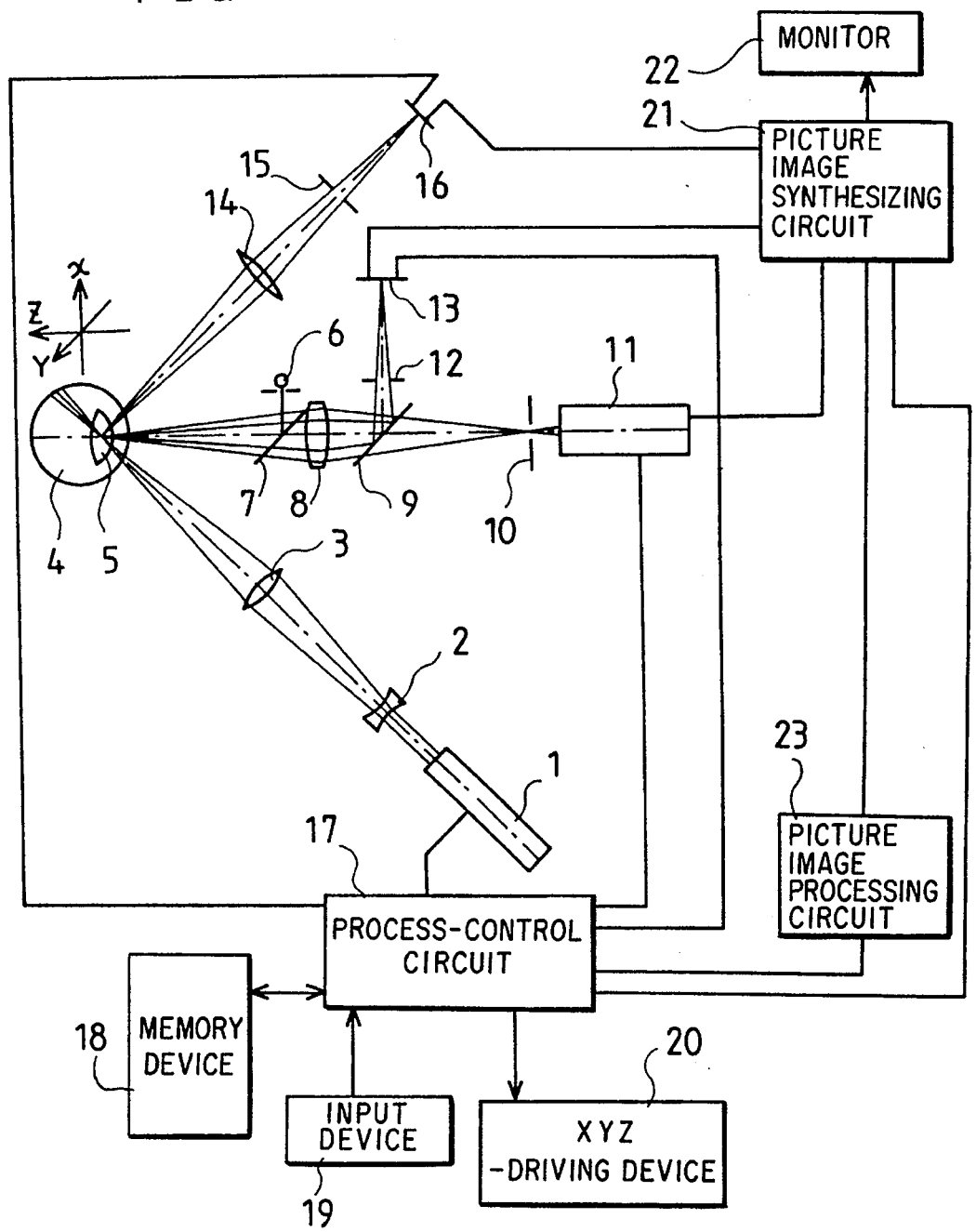
FIG. 1 is a schematic view of showing a whole composition of the apparatus in a first embodiment of the invention.

In the first embodiment of the present invention, FIG. 1 is a schematic view showing a whole composition of the ophthalmic apparatus for measuring the extent of opacity of a crystalline lens of an examinee's eye.

The apparatus comprises a laser projecting optical system, an alignment light projecting optical system, a laser dispersion light detecting optical system, a first alignment detecting optical system and a second alignment detecting optical system.

More specifically, the laser projecting optical system for measuring the extent of opacity of the eye 4 is constructed of a laser light source 1 for projecting a laser light to a crystalline lens 5 of an examinee's eye 4, an expander lens 2, and a condensing lens 3. The alignment light projecting optical system is constructed of a spot light source 6 and a half mirror 7, which projects alignment light to the eye 4. The laser dispersion light detecting optical system, which is for detecting a laser beam dispersed by the crystalline lens 5, is constructed of a focusing lens 8, a dichroic mirror 9, a diaphragm 10 having an aperture and a light receiving device 11. And the first alignment detecting optical system is constructed of a diaphragm 12, a two-dimensional CCD 13, which both are disposed on an optical axis branched off from the optical axis of the laser dispersion light detecting optical system, the focusing lens 8 and the dichroic mirror 9, and the second detecting optical system is constructed of a focusing lens 14, a diaphragm 15 and a two-dimensional CCD 16, an optical axis of which intersects at a predetermined angle with that of the laser dispersion light detecting optical system.

Signals generated at the light receiving device 11, the two-dimensional CCDs 13 and 16 are conducted respectively through predetermined processes and then input to a process-control circuit 17.

The apparatus is also provided with a memory means 18 for storing the coordinate and others of a measuring position, an input device 19 for inputting the ID number of the examinee and measuring date and so on, a XYZ driving device 20 for moving the optical systems with respect to the examinee's eye in three-dimensional directions, a picture image synthesizing circuit 21, a television monitor 22 and a picture image processing circuit 23.

Operation of the above constructed apparatus will be explained as follow.

First, the spot light source 6 for alignment is turned on to project alignment light through the half mirror 7 to a cornea of the eye 4. Light reflected by the surface of the cornea is incident into the first and the second alignment detecting optical systems respectively. And the cornea reflecting light beams are detected at the CCD 13 of the first alignment light detecting optical system and at the CCD 16 of the second alignment light detecting optical system respectively then.

Figure 2:
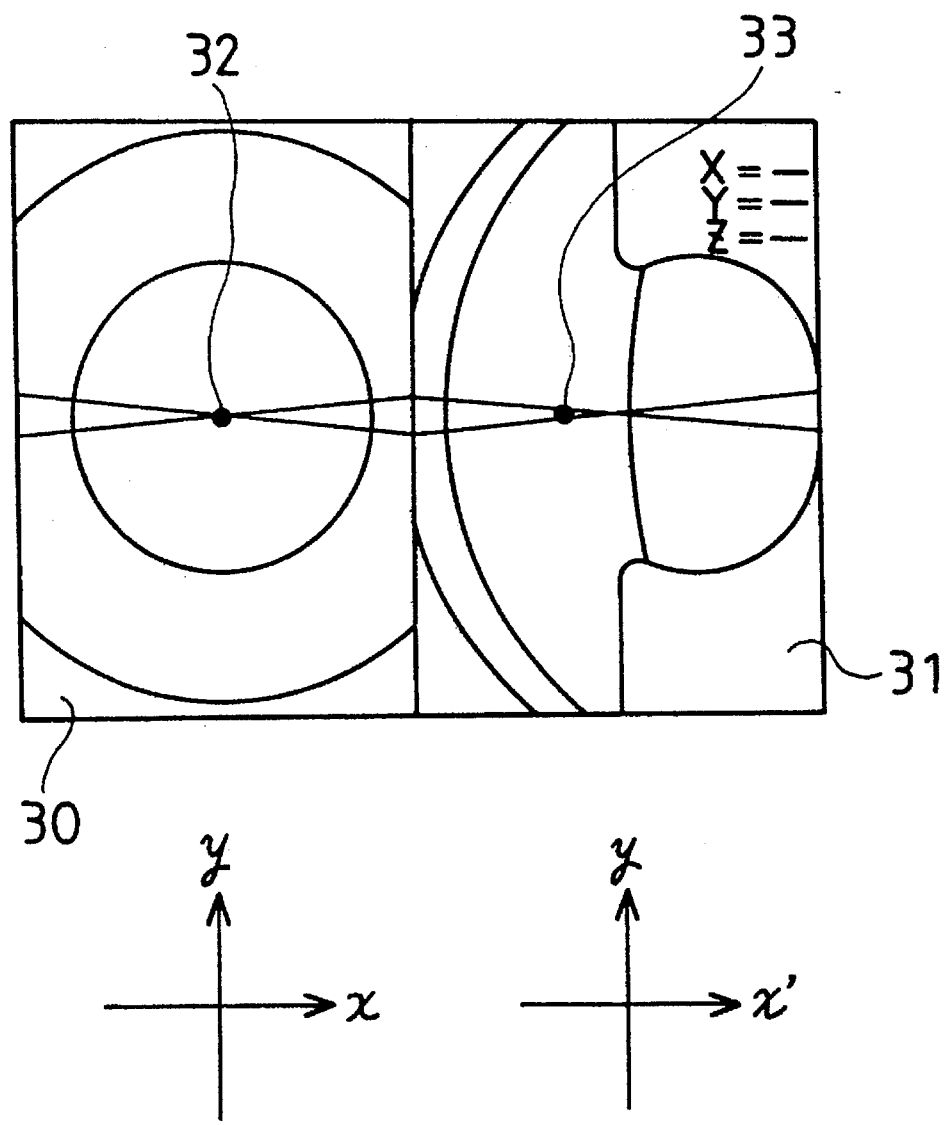
FIG. 2 is a schematic diagram of showing an example of displayed images on a monitor of the apparatus.

Information of picture images at the two-dimensional CCDs 13 and 16 are displayed through the picture image synthesizing circuit 21 on the monitor 22. An example of picture images are shown in FIG. 2 at right and left, the left picture 30 of which shows a picture image through the first alignment detecting system and the right picture 31 of which shows a picture image through second alignment detecting system. Luminescent spots 32 and 33 displayed on the respective pictures 30 and 31 indicate a cornea reflecting luminescent spot of the alignment light. The apparatus is so aligned in advance that luminescent spots 32 and 33 have higher luminance than a predetermined reference on the monitor display.

In the first alignment detecting optical system, the alignment light reflected by the cornea surface near a cornea apex of the eye 4 is passed through the half mirror 7 and the focussing lens 8, and is reflected by the dichroic mirror 9 toward the diaphragm 12. The light passed through the diaphragm 12 forms a luminescent spot, which is a cornea reflecting image of the alignment light, on the two-dimensional CCD 13. The picture image processing circuit 23 then detects a position of the luminescent spot 32 to find out the relative position of the apparatus in horizontal and vertical directions with respect to the eye 4.

Simultaneously, alignment light reflected by the cornea surface of peripheral area in the cornea surface is incident into the second alignment detecting optical system, wherein the alignment light is passed through the focussing lens 14 and the diaphragm 15, and forms a luminescent spot on the two-dimensional CCD 16. Picture image signal generated at the two-dimensional CCD 16 is then transmitted to and processed in the picture image processing circuit 23, so that the location of the luminescent spot 33 is detected. Based on the luminescent spot 33 and the position of the apparatus detected in the first alignment detecting optical system, the process-control circuit 17 calculates, a relative position of the apparatus in an optical axis direction of the eye 4 with respect to the eye 4.

Figure 3:
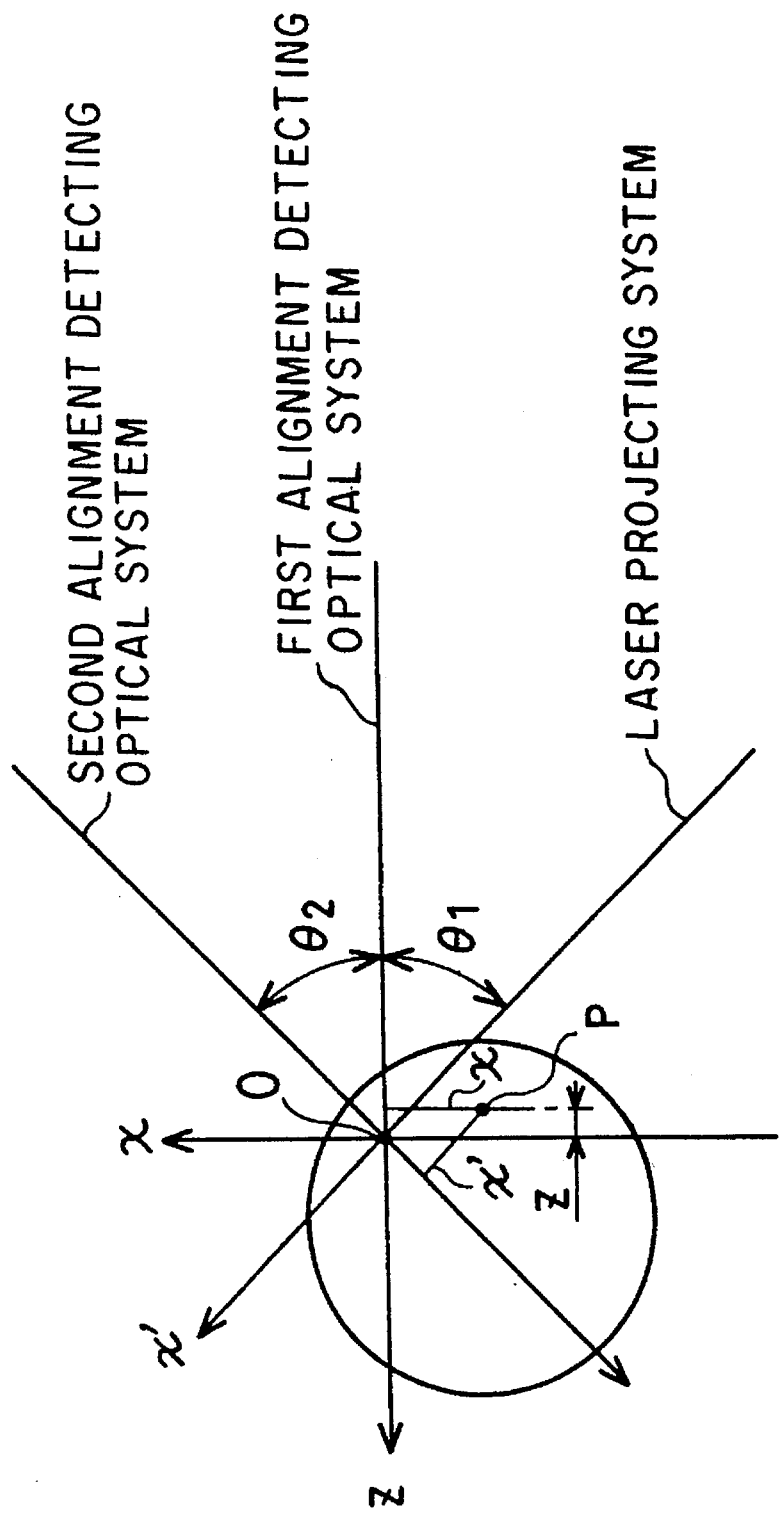
FIG. 3 is an explanatory view to find out a position of a measuring point in the first embodiment.

When assuming that an intersection point (measuring portion) of each optical axis of the first and the second alignment detecting optical systems and the laser projecting optical system is a reference point "O", a deviation between a cornea reflecting luminescent point P and the optical axis of the second alignment detecting optical system is "x'", an angle at which the optical axis of the second alignment detecting optical system crosses with the axis of the first alignment detecting optical system is "$\theta_2$", another angle at which the laser projecting optical system crosses with the same is "$\theta_1$", and a deviation along the optical axis of the first alignment detecting optical system between the reference point O and the cornea reflecting luminescent P is "z", as shown in FIG. 3, the deviation "z" is expressed by the following formula (I).

$$z = \frac{1}{\sin \theta_2} (x' - \cos \theta_2 \cdot X) \quad (I)$$

The deviation value of the apparatus with respect to the examinee's eye 4, which is found out through the above process, specifies coordinates in three-dimension of the current measuring portion, and those coordinates are displayed on the picture 31.

When the portion to be measured is determined as above, the laser source 1 emits laser light through the laser projecting optical system to the examinee's eye 4. The laser light is dispersed at the measuring portion, condensed at the focussing lens 8, and focuses on the diaphragm 10 after passing through the dichroic mirror 9. The dispersed laser light is passed through the diaphragm 10 which restricts a measurement area, and is detected on the light receiving device 11. By analyzing the intensity of the dispersed light detected on the light receiving device 11, the extent of opacity of the measured portion in the inside of the eye is measured.

The measured data are stored in the memory means 18, as well as input values including the ID number of the examinee and measurement date and others, and the positional coordinate of a measured portion of when trigger signal is generated.

Such information including the measured data may be stored in memory medium such as floppy and the like, besides in a storing circuit of the apparatus.

At the time of re-measurement, the coordinate of a measuring point is called by input of the ID number or the like of the examinee through the input means 19, or the coordinate may be input direct through the input means 19. The XYZ driving means 20 is operated based on the called coordinate to move automatically the apparatus itself to the alignment position. As the XYZ driving means, it is possible to use various known types of driving means, and also to utilize a three-dimensional moving mechanism known as joystick mechanism of ophthalmic apparatus which will be driven with motor and the like to move the apparatus. If detecting each position in each direction, more accurate alignment may be achieved. After alignment, the servo-mechanism of the apparatus is operated to fix automatically a setting position.

In the first embodiment, the optical axis of the first detecting optical system is coaxial with that of the alignment light source, but it is not necessary to be.

A second embodiment of the present invention will be described hereinafter.

In the second embodiment, two alignment detecting optical systems are arranged symmetrically about the visual axis of the eye 4. The alignment light projecting system is disposed partially on the visual axis of the eye 4, as well as in the first embodiment, while the laser dispersion light detecting optical system and the first alignment detecting optical system are arranged separately. While preserving the same angle as that in the first embodiment between the laser projecting optical system and the laser dispersion light detecting optical system, symmetrical arrangement of the laser projecting optical system and the laser dispersion light detecting optical system with respect to the visual axis of the eye can improve a problem that measurement light tends to be eclipsed in a small pupil of the examinee's eye with respect to the laser projecting system or the laser dispersion light detecting optical system.

Figure 4:
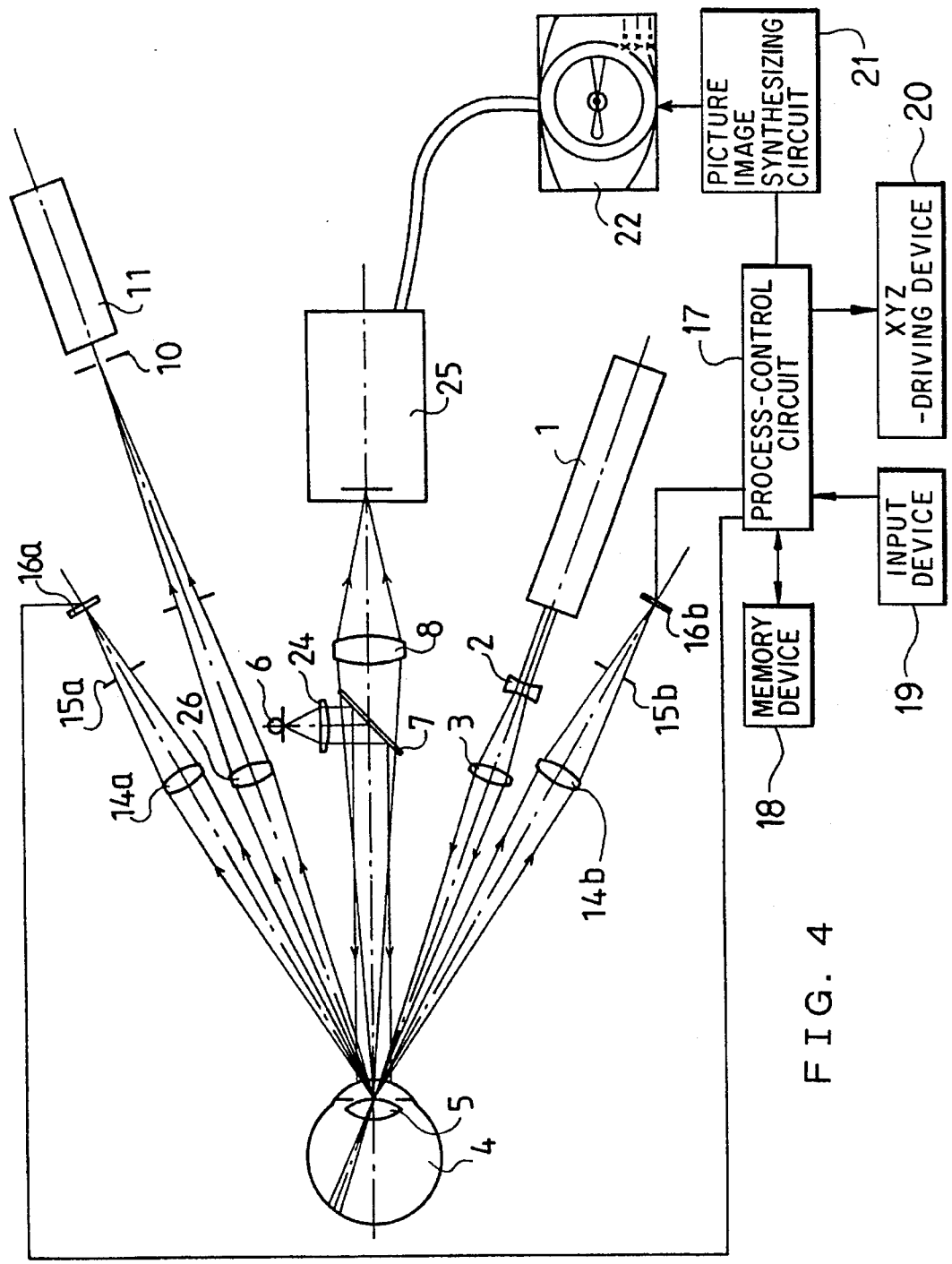
FIG. 4 is a schematic view of showing a whole composition of the apparatus in a second embodiment of the invention.

In the apparatus of the second embodiment, as shown in FIG. 4, the first alignment detecting optical system is constructed of a focusing lens 14b, a diaphragm 15b and a two-dimensional CCD 16b, the second alignment detecting optical system is constructed of a focusing lens 14a, a diaphragm 15a and a two-dimensional CCD 16a, an alignment observing system is constructed of the half mirror 7, the focusing lens 8 and a light receiving device 25, the laser dispersion light detecting system is constructed of a focusing lens 26, the diaphragm 10 and the light receiving device 11, and the alignment projecting system is provided with a collimating lens 24 for collimating alignment light in addition with the spot light source 6. The laser projecting system is the same as the first embodiment. The observing optical system is to observe the anterior part of the examinee's eye to perform rough alignment, also to observe the state of the laser beam incident inside the eye.

Detecting way of alignment deviation amount with the apparatus mentioned above is as follows.

Figure 5:
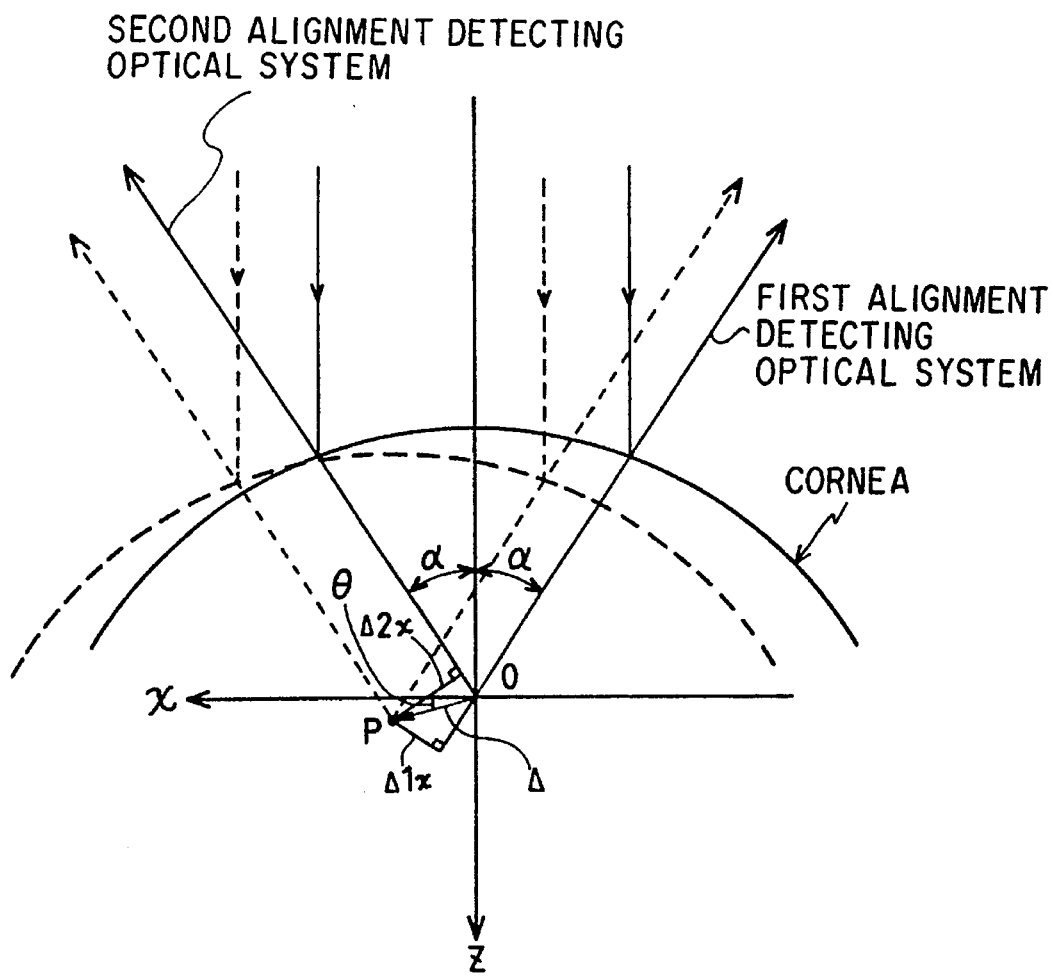
FIG. 5 is an explanatory view to find out a position of a measuring point in the second embodiment.

Assuming that each angle at which each optical axis of the first and the second alignment detecting optical systems crosses with an optical axis of the alignment projecting system is "α", as shown in FIG. 5, and that a cornea reflecting luminescent point "P" is deviated from an intersection point "O" of all optical systems, a coordinate (Δ, θ) of the cornea reflecting luminescent point "P" is found out based on respective coordinates (Δ1x, Δ1y), (Δ2x, Δ2y) of the first and the second alignment detecting optical systems, where (Δ, θ) is projection of three-dimensional deviation onto x-z plane.

Referring to FIG. 5, the following equations are given:

$$\Delta 1x = \Delta \sin(\pi/2 - \theta - \alpha) = \Delta \cos(\theta + \alpha)$$

$$\Delta 2x = \Delta \sin(\pi/2 + \theta - \alpha) = \Delta \cos(\theta - \alpha)$$

Based on those equations, the Δ and θ are found out by the following formulas:

$$\tan \theta = \frac{\Delta 2x - \Delta 1x}{\Delta 2x + \Delta 1x} \cdot \cot \alpha$$

$$\Delta = \frac{\Delta 1x + \Delta 2x}{2 \cos \theta \cos \alpha}$$

Converting this to a component in x, z directions, $$\Delta x = \Delta \cos \theta = \frac{\Delta 1x + \Delta 2x}{2 \cos \alpha}$$

$$\Delta z = \Delta \sin \theta = \frac{\Delta 2x - \Delta 1x}{2 \sin \alpha}$$

In y-axis direction, y deviation detected in the respective alignment detecting optical systems is expressed by Δy, which is given by the below equation:

$$\Delta y = 1y = \Delta 2y$$

As the described above, the three-dimensional alignment deviation (Δx, Δy, Δz) is detected based on the detected data at the first and the second alignment detecting optical systems.

Based on the three-dimensional alignment deviation of the apparatus with the examinee's eye, the coordinate of the current measuring portion in three-dimension is detected and displayed on the monitor 22 as well as the first embodiment. Examination of the eye following in a similar manner as the first embodiment, the detail thereof is omitted accordingly.

The present invention may be embodied in other specific forms without departing from the spirit or essential characteristics thereof.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for aligning optical systems thereof with an expected portion in the inside of an examinee's eye to examine the eye by examining means, the apparatus comprising:

an observing optical system for observing an anterior portion of the eye;

a light projecting optical system for projecting alignment light to a cornea of the eye;

a detecting optical system for detecting in two directions the light which is projected from the light projecting optical system and then reflected by the cornea;

position calculating means for calculating a three-dimensional position of the apparatus with respect to the eye, based on the detected data at said detecting optical system;

signal generating means for generating signals to carry out examination of the eye; and memory means for storing the three-dimensional position of the apparatus with respect to the eye at the time of signal generated at said signal generating means, as well as examination data.

2. The ophthalmic apparatus according to claim 1, wherein said projecting optical system projects a light beam through an alignment light reflecting member arranged in said observing optical system to the cornea of the eye.

3. The ophthalmic apparatus according to claim 1, wherein said observing optical system comprises a two-dimensional photo-detecting element and a display for displaying a photo image by the photo-detecting element, the two-dimensional photo-detecting element is used in common in one of said detecting optical systems.

4. The ophthalmic apparatus according to claim 1, further comprises a laser projecting optical system for projecting a laser beam to a crystalline lens of the examinee's eye, and a laser dispersion light detecting optical system for detecting a laser beam dispersed by the crystalline lens.

5. The ophthalmic apparatus according to claim 4, wherein said laser projecting optical system and said laser dispersion light detecting optical system each have optical axes which are symmetrical about the optical axis of said observing optical system.

6. An ophthalmic apparatus for aligning optical systems thereof with an expected portion in the inside of an examinee's eye to examine the eye, the apparatus comprising:

an observing optical system for observing an anterior portion of the eye;

a light projecting optical system for projecting alignment light to a cornea of the eye;

a detecting optical system for detecting the light projected from the light projecting optical system and reflected by the cornea, in two directions;

position calculating means for calculating a three-dimensional position of the apparatus with respect to the eye, based on the detected data at said detecting optical system;

examination portion determining means for determining the coordinate of a portion to be examined; and moving means for moving said examining means with respect to the examinee's eye, based on positional data provided by said measuring portion determining means and said position calculating means.

* * * * *